(12) United States Patent
Bell et al.

(10) Patent No.: US 7,748,124 B1
(45) Date of Patent: Jul. 6, 2010

(54) SCALPEL ASSEMBLY

(75) Inventors: Michael S. G. Bell, Ottawa (CA); Leonard G. Lee, Almonte (CA); Michael T. O'Malley, Appleton (CA); Timothy J. Maxwell, Kanata (CA)

(73) Assignee: Canica Design, Inc., Ottawa, Ontario (CA)

( * ) Notice: Subject to any disclaimer, the term of this patent is extended or adjusted under 35 U.S.C. 154(b) by 0 days.

(21) Appl. No.: 09/937,542

(22) PCT Filed: Apr. 7, 2000

(86) PCT No.: PCT/IB00/00426

§ 371 (c)(1),
(2), (4) Date: Sep. 26, 2001

(87) PCT Pub. No.: WO00/61014

PCT Pub. Date: Oct. 19, 2000

Related U.S. Application Data (60) Provisional application No. 60/128,529, filed on Apr. 9, 1999.

(51) Int. Cl.
*A61B 17/32* (2006.01)
(52) U.S. Cl. ........................................ 30/327
(58) Field of Classification Search ........... 606/167, 606/170, 172, 174, 181, 182; 30/339, 337, 30/340, 329, 327; 604/22, 166.01; 279/46.4, 279/56
See application file for complete search history.

(56) References Cited

U.S. PATENT DOCUMENTS

| | | | |
|---|---|---|---|
| 1,624,640 A | 4/1927 | Tietz | |
| 1,940,855 A * | 12/1933 | Friedman | 279/24 |
| 3,187,431 A | 6/1965 | Mattes | |
| 3,262,205 A * | 7/1966 | Arden | 30/338 |
| 3,609,864 A | 10/1971 | Bassett | |
| 3,706,106 A | 12/1972 | Leopoldi | |
| 3,798,688 A | 3/1974 | Wasson | |
| 3,877,147 A * | 4/1975 | Cummings | 30/329 |
| D258,310 S | 2/1981 | LaHaye | |
| D263,445 S | 3/1982 | Gordin et al. | |
| 4,389,778 A | 6/1983 | Hakansson | |
| 4,522,206 A * | 6/1985 | Whipple et al. | 606/174 |
| 4,646,440 A | 3/1987 | Decker | |
| 4,649,919 A * | 3/1987 | Thimsen et al. | 606/80 |
| 4,660,287 A | 4/1987 | Decker | |
| 4,922,614 A | 5/1990 | Machida | |
| 4,941,232 A | 7/1990 | Decker et al. | |
| 4,960,419 A * | 10/1990 | Rosenberg | 606/45 |
| 5,207,969 A | 5/1993 | Matwijcow | |

(Continued)

FOREIGN PATENT DOCUMENTS

CA 2 128 120 1/1996

(Continued)

*Primary Examiner*—Todd E Manahan
*Assistant Examiner*—Victor X Nguyen
(74) *Attorney, Agent, or Firm*—Kilpatrick Stockton LLP; John S. Pratt; Camilla C. Williams (57) ABSTRACT

A scalpel assembly utilizing an ejectable blade allowing easy installation and removal of the blade. Use of an ejectable blade permits a used or contaminated blade to fall freely from the scalpel assembly without direct contact with the blade.

33 Claims, 8 Drawing Sheets

U.S. PATENT DOCUMENTS

| | | | |
|---|---|---|---|
| 5,250,063 A * | 10/1993 | Abidin et al. ............... 606/167 |
| D345,290 S | 3/1994 | Sauber |
| 5,312,429 A | 5/1994 | Noack |
| 5,314,417 A * | 5/1994 | Stephens et al. ............ 604/264 |
| 5,423,843 A | 6/1995 | Werner |
| 5,431,672 A | 7/1995 | Cote et al. |
| 5,496,340 A | 3/1996 | Abidin et al. |
| 5,531,754 A | 7/1996 | Shackelford, Sr. et al. |
| 5,571,127 A | 11/1996 | DeCampli |
| 5,662,669 A | 9/1997 | Abidin et al. |
| 5,695,511 A * | 12/1997 | Cano et al. ................. 606/170 |
| 5,702,397 A * | 12/1997 | Goble et al. ................ 606/232 |
| 5,752,968 A * | 5/1998 | Jolly et al. ................. 606/167 |
| 5,779,724 A * | 7/1998 | Werner ....................... 606/167 |
| 5,792,162 A | 8/1998 | Jolly et al. |
| 5,867,912 A * | 2/1999 | Hickok et al. ................ 30/329 |
| 5,908,432 A | 6/1999 | Pan |
| 5,924,206 A * | 7/1999 | Cote et al. ................... 30/337 |
| 5,938,675 A | 8/1999 | Gharibian |
| 5,938,676 A | 8/1999 | Cohn et al. |
| 5,957,945 A * | 9/1999 | Bays .......................... 606/180 |
| 5,984,918 A * | 11/1999 | Garito et al. ................... 606/41 |
| 6,022,364 A | 2/2000 | Flumene et al. |
| 6,228,097 B1 * | 5/2001 | Levinson et al. ........... 606/142 |
| 6,402,770 B1 * | 6/2002 | Jessen ........................ 606/170 |
| 6,626,925 B2 | 9/2003 | Newman et al. |
| 6,629,985 B1 | 10/2003 | Kiehne |
| 6,757,977 B2 | 7/2004 | Dambal et al. |
| 6,949,109 B2 | 9/2005 | Iske et al. |
| 2004/0098001 A1 | 5/2004 | Holman |
| 2005/0065541 A1 | 3/2005 | Abidin et al. |

FOREIGN PATENT DOCUMENTS

| | | |
|---|---|---|
| CA | 2167120 | 2/2000 |
| CH | 84163 | 6/1919 |
| DE | 1144437 | 2/1963 |
| DE | 297 03 402 | 4/1997 |
| WO | WO 0061014 | 10/2000 |
| WO | WO 03/068079 | 8/2003 |
| WO | WO 2004/045428 | 6/2004 |
| WO | WO 2005/089202 | 9/2005 |

* cited by examiner

SCALPEL ASSEMBLY

RELATED APPLICATION DATA

This application claims priority under U.S. law to U.S. Patent Application No. 60/128,529 filed Apr. 9, 1999, entitled "Scalpel Assembly" which is hereby incorporated by reference.

BACKGROUND OF THE INVENTION

1. Field of the Invention

This invention relates to a scalpel having a releasable, detachable or disposable blade and a reusable scalpel assembly.

2. Description of Related Art

Surgical scalpels have long been available, including such devices utilizing detachable or disposable blades that have a keyed or keyhole shaped slot. There is a need for a scalpel with better ergonometric properties. In addition, there is a need for a scalpel assembly that allows easy installation of a blade and that allows easy, safe release of a detachable or disposable blade and that can be manipulated with one hand. There is also a need for such a scalpel assembly to be durable and able to withstand repeated autoclaving and other sterilization techniques.

SUMMARY OF THE INVENTION

This invention is a scalpel assembly for disposable or detachable blades ejectable with the push of a button. This allows a used or contaminated blade to fall freely from the scalpel assembly into a disposal receptacle, such as a sharps container, without direct contact of medical personnel with the used or contaminated blade. A conventional disposable or detachable blade having a keyed slot is utilized and engaged by a blade bar that extends from a handle assembly. This blade bar may be extended with one hand by manipulating a push button or other actuator, releasing the blade from the handle. The push button is located on the handle remote from the blade, so that contact between the user's fingers and the blade is unnecessary and unlikely.

Accordingly, it is a feature of this invention to provide a scalpel assembly that allows release of a blade without requiring medical personnel to touch the blade.

It is a further feature of this invention to provide a scalpel assembly that allows release of a blade by manipulation with one hand.

Another feature of this invention is to provide a scalpel assembly that allows easy blade installation.

It is another feature of this invention to provide a scalpel assembly that is durable, and capable of withstanding repeated sterilization.

Another feature of this invention is to provide a scalpel assembly with desirable ergonometric properties.

This invention can be better understood by reference to the Brief Description of the Drawings, which should not be interpreted to limit the scope thereof.

DETAILED DESCRIPTION

This invention relates to a scalpel having an easily detachable, optionally disposable blade that can be removed by actuation of a button with the same hand holding the scalpel assembly. This eliminates the need for medical personnel to handle or touch the blade after the blade has come into contact with surgical patients or their body fluids.

The scalpel is an ergonomic surgical instrument, and the disposable or detachable scalpel blade need be handled only when it is sterile and is being attached to the scalpel assembly, if at all. In a more particular embodiment of this invention, the scalpel assembly comprises an attachment mechanism for receiving and engaging a disposable or detachable scalpel blade, and may desirably be adapted to receive and engage conventional scalpel blades. As used in the description of the scalpel assembly of this invention, a proximal end is one nearer to the blade tip and a distal end is one remote from the blade tip.

The scalpel assembly includes a handle body, which provides a surface for the surgeon or medical personnel to grip the scalpel during transport or use. A button assembly inside the handle body serves to allow attachment and detachment of the blade from the scalpel assembly. The handle assembly is made up of a collet core, a collet, a handle body, and a button retainer. The collet houses the collet core. The proximal end of the handle body is attached to the collet. The interior surface of the distal end of the handle body is adapted to receive and engage the proximal end of the button retainer after the button assembly is inserted into the handle assembly. The button assembly is made up of a blade bar, a spring, which may be tapered, a push rod, and a button. The blade bar contains a groove and heel forming a tang, which allows it to engage a blade. The proximal end of the spring engages the interior of the handle assembly, desirably toward the proximal end. For example, the spring may engage the distal end of the collet. The distal end of the spring is engaged by the push rod. The distal end of the blade bar is engaged with the proximal end of the push rod. The proximal end of the button is attached to the distal end of the push rod. Alternatively, two or more of the button, the push rod and the blade bar may be an integral component. Depression of the button compresses the spring and extends the blade bar, disengaging the blade. In alternative embodiments, the push rod may be actuate by a button, lever, slide or other mechanism located intermediate the ends of the handle rather than at the handle's distal end.

This invention is described below by reference to the drawings; however, it should be understood that the drawings are directed to a specific embodiment of the invention and do not limit the scope thereof.

Figure 1:
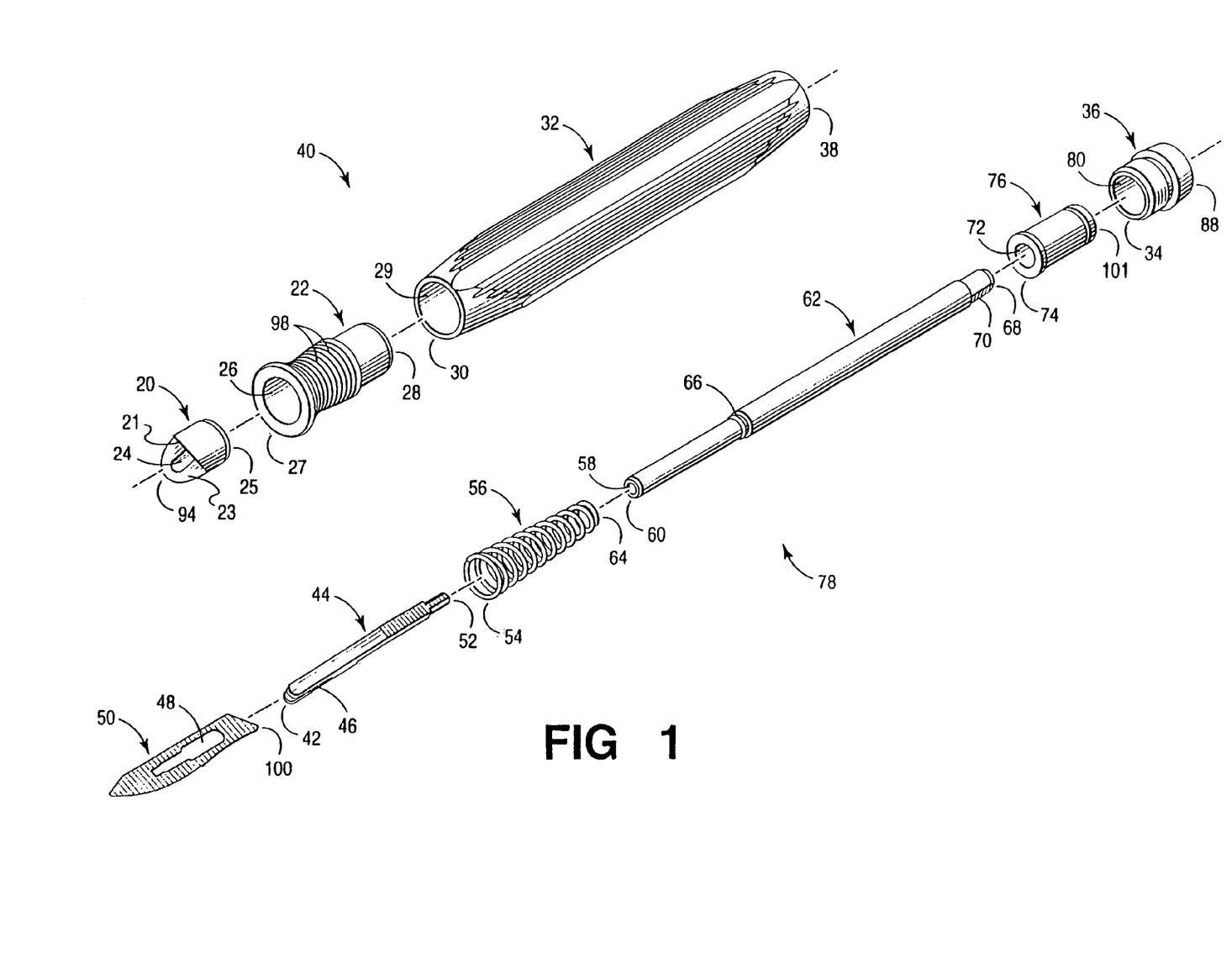
FIG. 1 is an exploded perspective view of one embodiment of the scalpel handle assembly of this invention.
Figure 2:
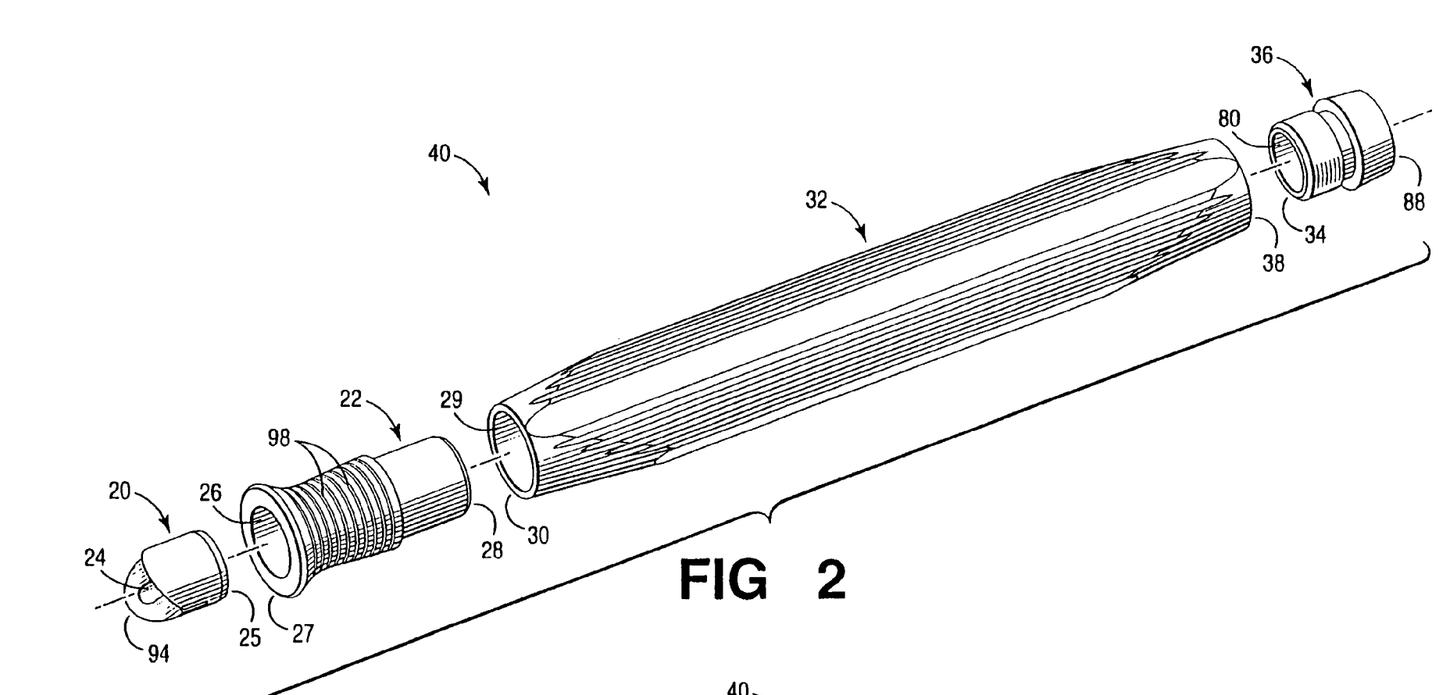
FIG. 2 is an exploded perspective view of the handle body assembly of the scalpel assembly shown in FIG. 1.
Figure 3:
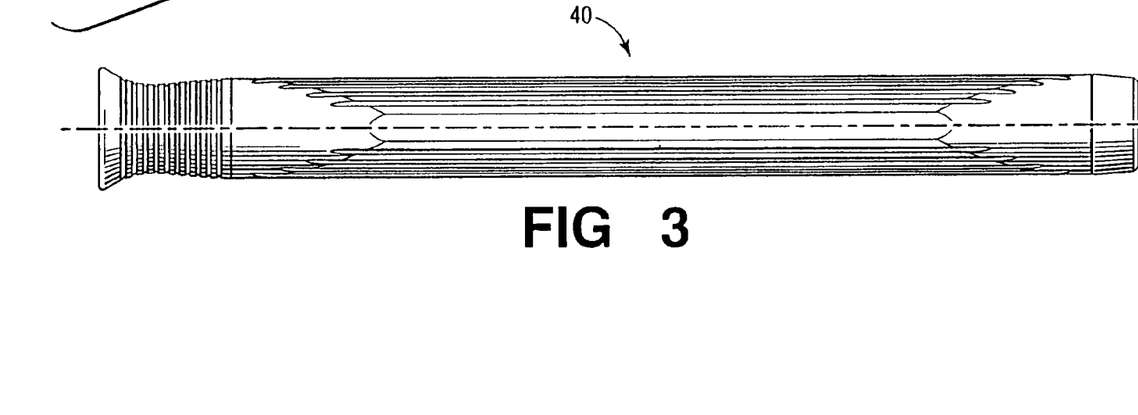
FIG. 3 is a side elevation view of the assembled handle body assembly of FIG. 2.

As shown in FIG. 1, the scalpel assembly 86 of one embodiment of this invention includes a handle body assembly 40 and a button assembly 78. The handle body assembly of this embodiment contains collet core 20 housed within collet 22. Collet core 20 is penetrated by bore 24, which provides for movement of blade bar 44 in and out of, and laterally within, collet core 20 during engaging and releasing of the blade 50 in response to depressing button 76. Collet core 20 also contains a pair of sloping front surfaces 21 and 23. Collet core 20 is inserted into collet hole 26 of collet 22 with a press fit, as shown in FIGS. 2 and 3. Distal end 28 of collet 22 is inserted into body bore 29 at proximal end 30 of handle body 32 with a press fit, as shown in FIGS. 2 and 3. In an alternative embodiment, either the button assembly, the handle body assembly, or both, may be manufactured as a single unit. Proximal end 34 of button retainer 36 is connected to distal end 38 of handle body 32.

Figure 6:
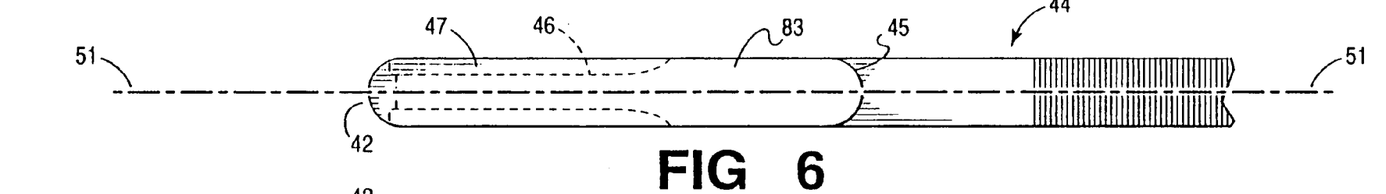
FIG. 6 is a top plan view of the proximal portion of the blade bar of this invention.
Figure 7:
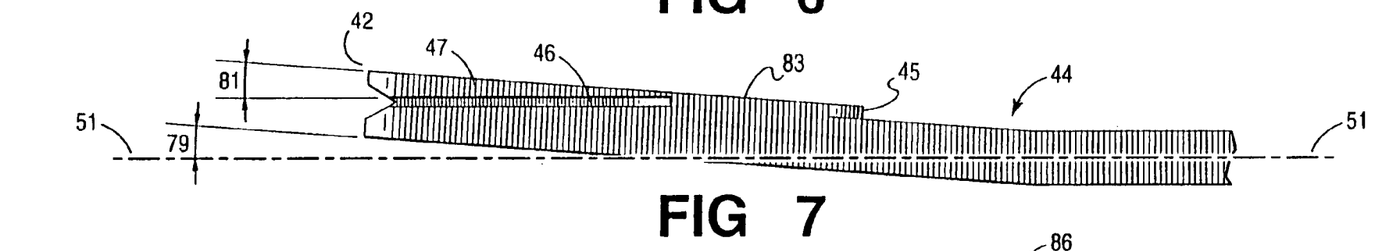
FIG. 7 is a side elevation of the proximal portion of the blade bar of this invention.

The button assembly 78 contains blade bar 44, tapered coiled spring 56, push rod 62, and button 76. As best shown in FIGS. 6 and 7, proximal end 42 of blade bar 44 contains a groove 46. Grove 46 in the proximal end 42 of blade bar 44 and extending along portions of two of the blade bar's opposed sides, and a heel 45, define a tang 47 that is received in keyed slot 48 in blade 50. When tang 47 is inserted in keyed slot 48 of blade 50, the narrower portion of keyed slot 48 engages the unshaped groove 46 in proximal end 42 of blade bar 44.

Figure 4:
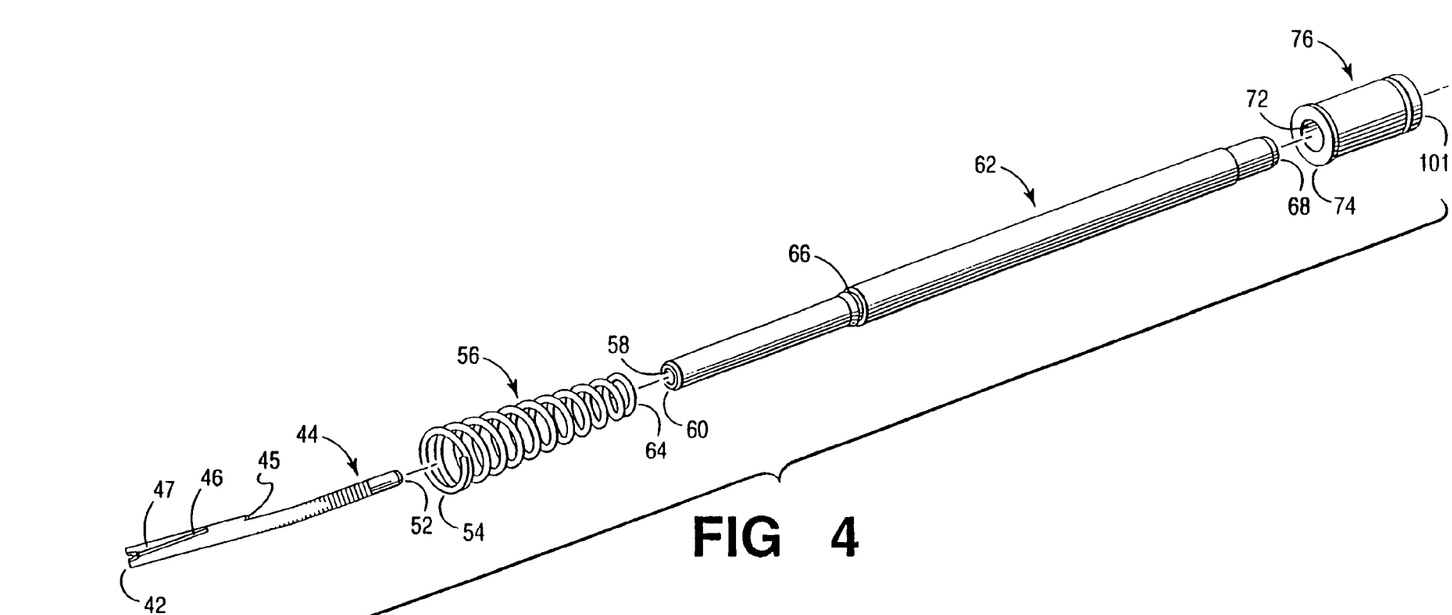
FIG. 4 is an exploded perspective view of a button assembly forming a part of the scalpel assembly of one embodiment of this invention.

Reduced diameter distal end 52 of blade bar 44 enters proximal end 54 of tapered coiled spring 56, telescopes through tapered coiled spring 56, and is received in push rod bore 58 in proximal end 60 of push rod 62. Tapered coiled spring 56 is telescopingly connected to proximal end 60 of push rod 62, so that smaller diameter distal end 64 of tapered coiled spring 56 is captured by notch 66 on push rod 62. As shown in FIGS. 1 and 4, distal end 68 of push rod 62 contains a recess or flat surface 70. This recess 70 allows air to escape when reduced diameter distal end 68 of push rod 62 is telescopingly inserted into button bore 72 in proximal end 74 of button 76.

Figure 5:
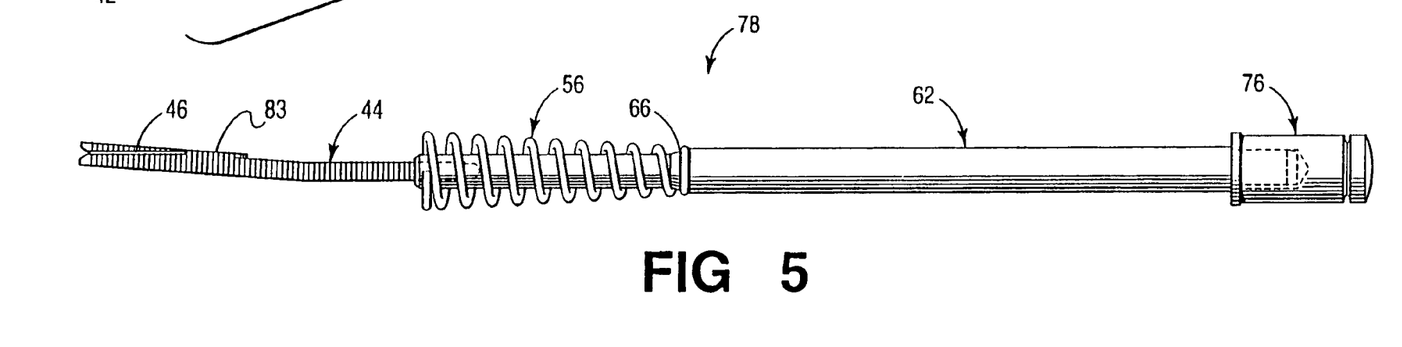
FIG. 5 is a side elevation assembly view of the button assembly of FIG. 4.
Figure 8:
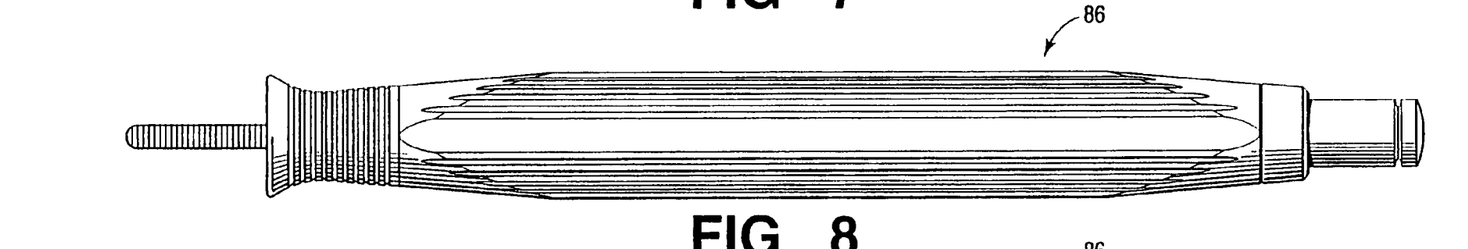
FIG. 8 is a top plan view of the scalpel assembly of FIG. 1.
Figure 9:
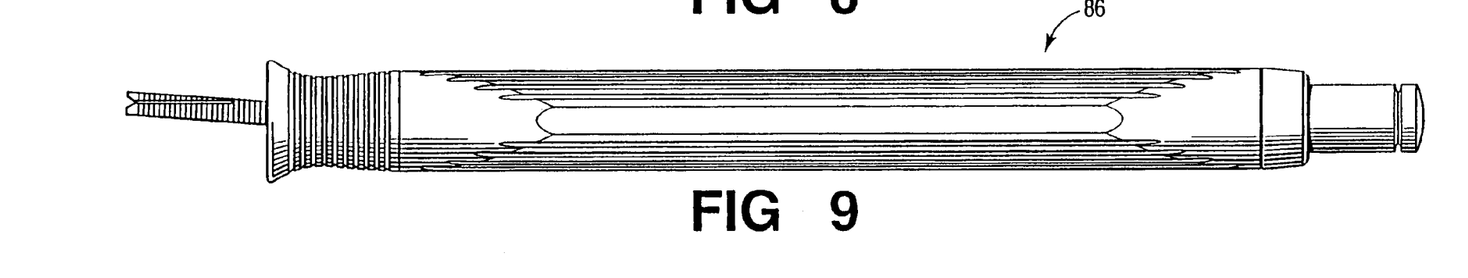
FIG. 9 is a side elevation view of the scalpel assembly of FIG. 1.

FIGS. 4 and 5 illustrate how blade bar 44, tapered coiled spring 56, push rod 62 and button 76 combine to form button assembly 78. Blade bar 44 is formed at an angle 79 to allow blade 50 to be freely inserted or removed in the extended position of the scalpel assembly, and held in place on blade bar 44 upon retraction, further described below. Button assembly 78, shown in FIG. 5, is inserted into handle assembly 40, shown in FIG. 3, before button retainer 36 is connected to distal end 38 of handle body 32. Button retainer 36 is then connected to distal end 38 of handle body 32 so that button 76 passes through button retainer bore 80. Proximal end 34 of button retainer 36 is threadedly connected to distal end 38 of handle body 32. Proximal end 74 of button 76 is held in place in handle body 32 by button retainer 36. Scalpel assembly 86 is shown in FIGS. 8 and 9.

Figure 10:
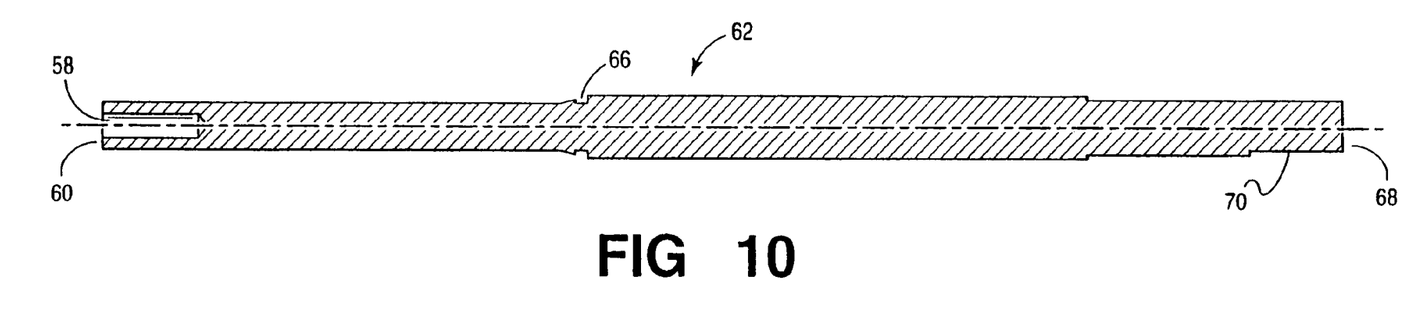
FIG. 10 is a longitudinal section view of the push rod shown in FIG. 1.
Figure 11:
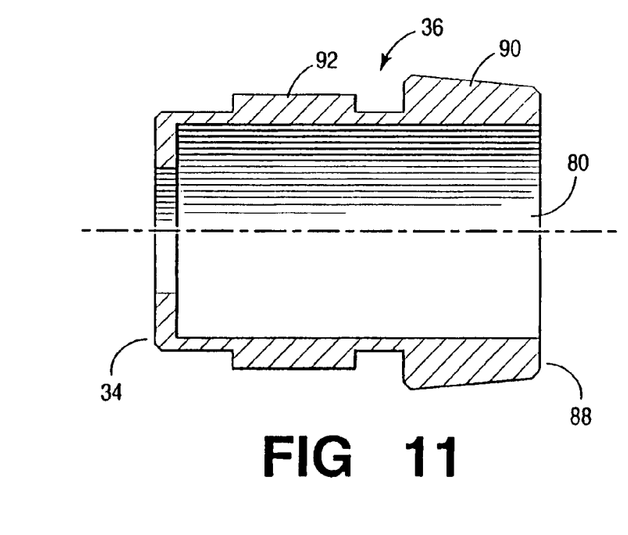
FIG. 11 is a side elevation section view of the button retainer shown in FIG. 1.
Figure 12:
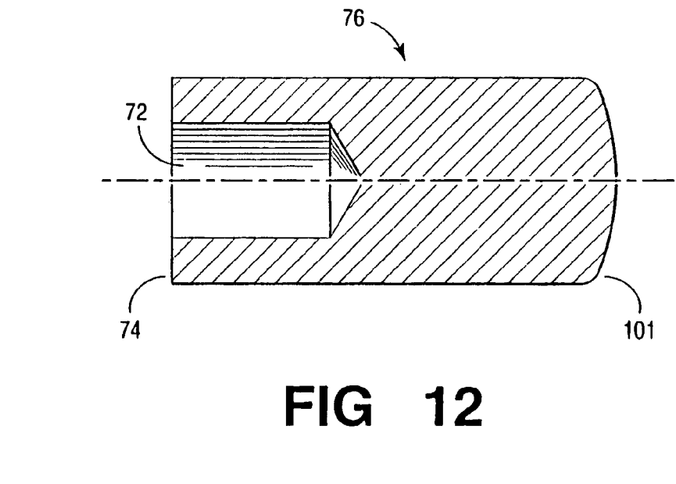
FIG. 12 is a side elevation view in section of the button shown FIG. 1.

FIG. 10 shows push rod 62. Push rod bore 58 is located at proximal end 60 of push rod 62. Recess 70 is located at distal end 68 of push rod 62. Push rod 62 has annular depression or notch 66. As shown in FIG. 11, distal end 88 of button retainer 36 can be knurled to make disassembly easier. Threads 92 on button retainer 36 allow button retainer 36 to be joined to distal end 38 of handle body 32. FIG. 12 shows button 76, which has button bore 72 at proximal end 74.

Figures 13, 14, 15:
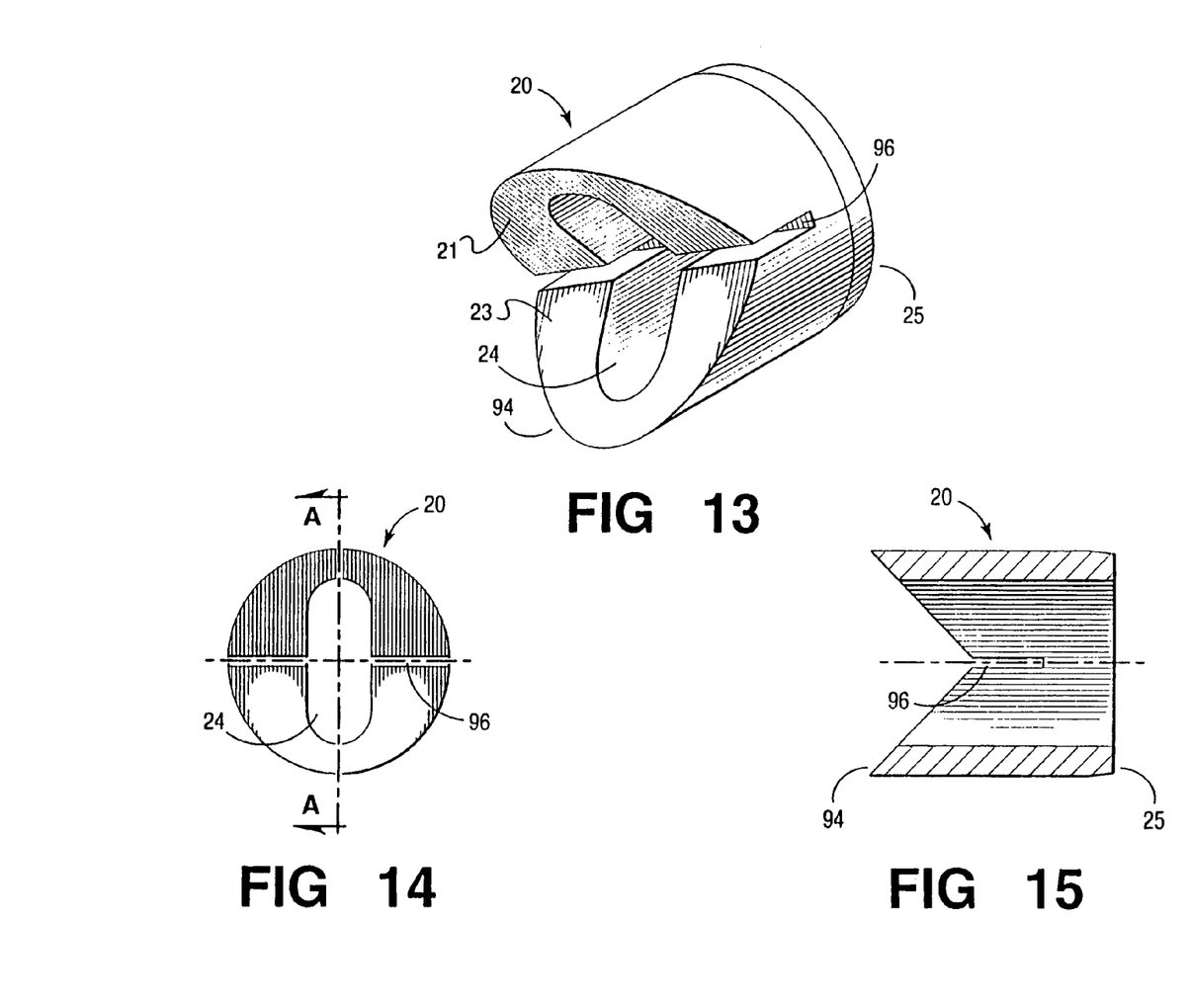
FIG. 13 is a perspective view of a collet core forming part of the handle body assembly shown in FIG. 8.
FIG. 14 is an end elevation view of the collet core of FIG. 13.
FIG. 15 is a side elevation section view of the collet core of FIG. 13.
Figure 16:
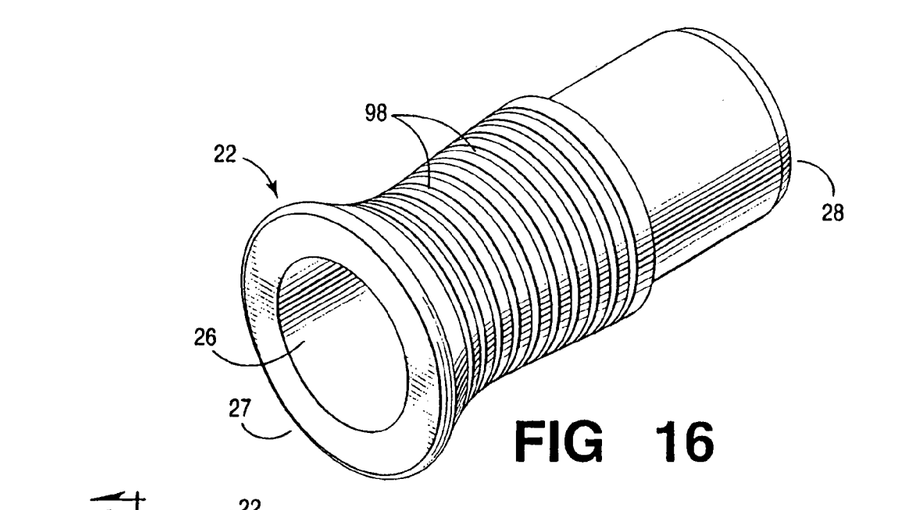
FIG. 16 is a perspective view of the collet of the handle body assembly of FIG. 2.
Figure 17:
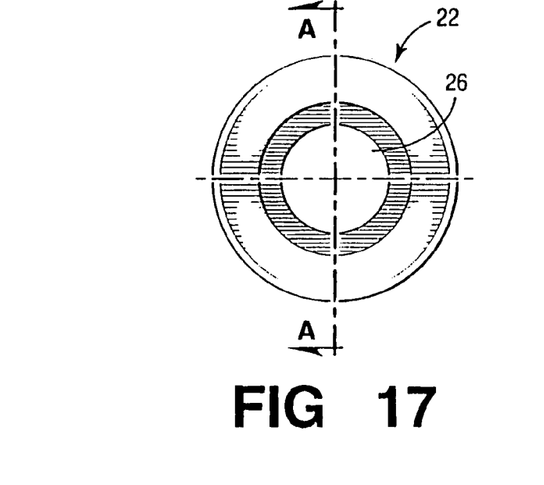
FIG. 17 is an enlarged end elevation view of the collet of FIG. 16.
Figure 18:
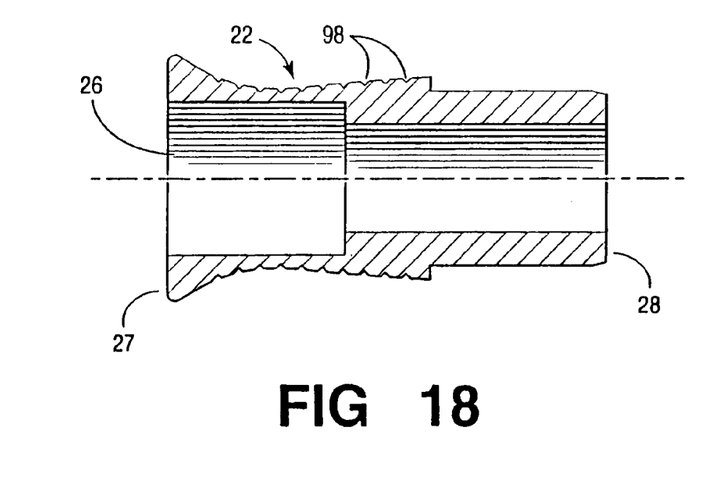
FIG. 18 is a side elevation section view of the collet of FIG. 16.

FIGS. 13, 14 and 15 depict collet core 20. Proximal end 94 of collet core 20 contains longitudinally oriented, centered slit 96 positioned transverse to the wider dimension of bore 24. Collet core 20 has collet core bore 24 that has a greater height (in FIG. 14) than width and may be oval as shown, rectangular or another appropriate shape that confines side-to-side bar movement along slit 96 and permits such movement transverse to slit 96. Collet 22 is depicted in FIGS. 16, 17 and 18. FIGS. 16 and 18 show threads 98 on collet 22.

Retraction of blade bar 44 secures blade 50 by positioning distal end 100 of blade 50 within slit 96 of collet core 20, so that blade 50 is held in place on blade bar 44. Blade bar angle 79 allows blade 50 to be inserted and removed from blade bar 44 when the handle is in an extended position, and holds blade 50 in place, coaxial with or parallel to the longitudinal axis of the handle, upon retraction. As can best be seen in FIGS. 6 and 7, blade bar 44 is bent so that proximal end 42 is at an acute angle 79 relative to distal end 52 (and the longitudinal axis 51 of the button assembly 78 and scalpel assembly 86). Groove 46 is positioned at an acute angle 81 (at least approximately equal to angle 79) relative to the tang face 83 of blade bar 44. This causes blade 50 to be at least approximately coaxial with the longitudinal axis of scalpel assembly 86 when blade 50 is secured in scalpel handle assembly 86.

Collet core 20 has slit 96, which traps blade 50 upon retraction. Front surfaces 21 and 23 each slope toward slit 96, thereby serving to guide distal end 52 of blade bar 44 into slit 96 when blade bar 44 retracts into collet core bore 24, drawing blade 50 back with it. The oval shape of bore 24 allows blade bar 44 to move perpendicular to slit 96 as blade bar 44 is guided into slit 96 by one or both of the pair of front surfaces 21 and 23. The slit urges the distal end of blade 50 toward blade bar 44, thereby retaining the keyed slot 48 in blade 50 on heel 45 of tang 47. Tapered coiled spring 56 retracts the blade bar 44, securing blade 50 in the scalpel assembly 86 while the flared larger diameter end of spring 58 permits the above-described lateral movement of blade bar 44.

Blade 50 may be released with one hand by pressing of button 76. Depression of button 76 forces blade bar 44 out of proximal end 94 of collet core 20 so that blade 50 is discharged from slit 96 in collet core 20 and blade 50 disengages from blade bar 44. This allows easy installation and push button ejection of blade 50.

This invention may be formed from any durable metals, including aluminum, stainless steel, and autoclavable plastics. The scalpel may be made in any desired size, although typical handle lengths range between 3.5 and 6 inches and typical handle diameters range between 0.330 and 0.750 inch.

The shape of the handle may vary from full round to oval or multi-faceted shapes in order to suit a range of ergonomic considerations.

Figure 19:
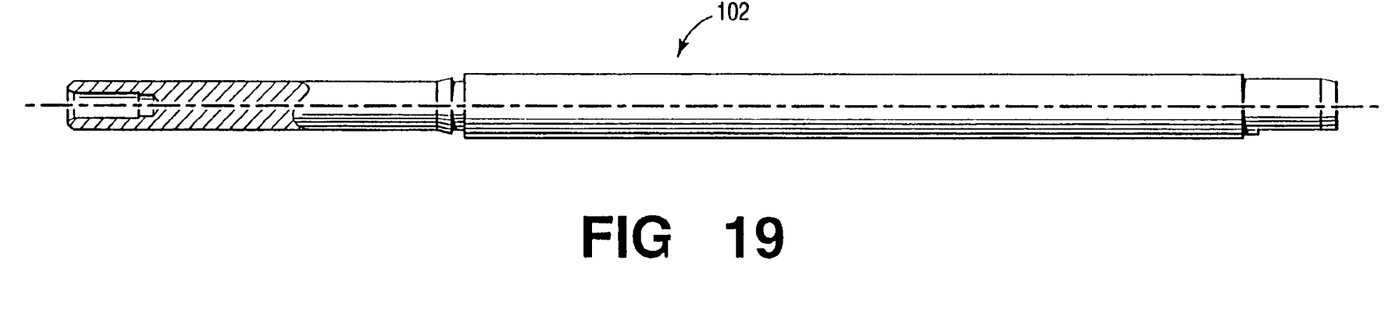
FIG. 19 is a side elevation view of a push rod forming part of the button assembly of an alternative embodiment of this invention.
Figure 20:
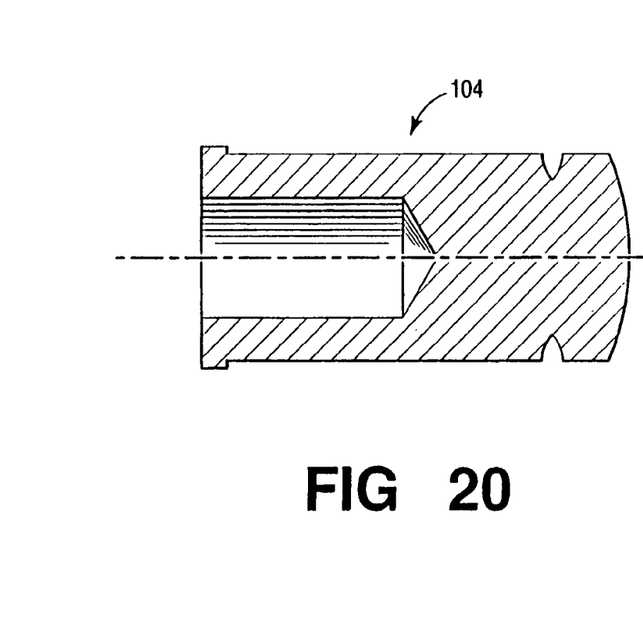
FIG. 20 is a side elevation section view, in section, of the button forming part of a button assembly of an alternative embodiment of this invention.
Figure 21:
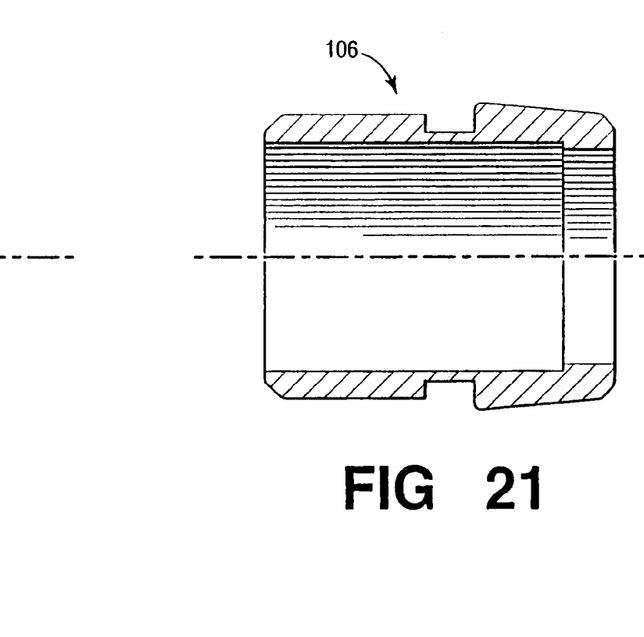
FIG. 21 is a side elevation view, in section, of the button retainer forming part of the handle assembly of an alternative embodiment of this invention.

FIG. 19 depicts an alternative push rod 102, for use in the scalpel assembly of this invention. FIG. 20 depicts an alternative button 104, for use in the scalpel assembly of this invention. FIG. 21 depicts an alternative button retainer 106 for use in the scalpel assembly of this invention.

The invention has been described by reference to specific embodiments, but is not limited to these embodiments. The invention extends to all variations and equivalents thereof within the scope of the following claims, as would be apparent to those of skill in the art.

The invention claimed is:

1. A handle assembly for a detachable scalpel blade having a keyed slot, the handle assembly comprising:
   (a) a handle body having a longitudinal axis,
   (b) protruding from the handle body a blade bar having a tang for insertion in the keyed slot, and a groove in the protruding portion of the bar
   (c) a spring for urging the distal end of the blade bar into the handle body, and
   (d) a collet,
   wherein the bar is bent and the groove is approximately parallel to the longitudinal axis.

2. The assembly of claim 1, wherein the blade is received in the groove in the protruding portion of the bar.

3. The assembly of claim 1, wherein the spring comprises a tapered, coiled spring.

4. The assembly of claim 1, wherein the bar is coupled to an actuator for urging the protruding portion of the bar out of the handle assembly for removing the blade from the bar or mounting the blade on the bar.

5. The assembly of claim 4, wherein the actuator is a button attached to a rod attached to the bar.

6. The assembly of claim 5, wherein the rod has two ends and the bar attaches to one end and the button attaches to the other end.

7. The assembly of claim 1, wherein the handle body further comprises:
   (a) a handle grip, and
   (b) a collet core.

8. The assembly of claim 7, wherein the handle grip has a generally oval cross-sectional shape.

9. The assembly of claim 7, wherein the handle grip further comprises ribs.

10. The assembly of claim 7, wherein the collet has a proximal end and wherein the collet flares at its proximal end.

11. The assembly of claim 1 further comprising a retainer for capturing a rod within the handle body.

12. The assembly of claim 11, wherein the retainer is attached to the handle body with mating threads.

13. The assembly of claim 1, wherein the collet further comprises a through bore within which the blade bar is positioned.

14. The assembly of claim 13, wherein the collet core further comprises a slit.

15. The assembly of claim 14, wherein the collet core further comprises at least one face sloping toward the slit.

16. The assembly of claim 13, wherein the at least one sloping face guides the blade end into the slit thereby preventing the blade from disengaging from the heel.

17. The assembly of claim 13, wherein the bore is sized and shaped to permit the bar to move laterally along one axis orthogonal to the longitudinal axis.

18. The assembly of claim 13, wherein the bore has a generally oval cross-sectional shape so that the bar can move laterally within the bore along one axis orthogonal to the longitudinal axis.

19. The assembly of claim 1, wherein the tang is defined by a groove and a heel.

20. A handle assembly for a detachable scalpel blade having a keyed slot, the handle assembly comprising:
   (a) a handle body having a longitudinal axis and a handle grip,
   (b) protruding from the handle body a blade bar having a tang for insertion in the keyed slot,
   (c) a spring for urging the distal end of the blade bar into the handle body,
   (d) a collet having a proximal end, and a through bore within which the blade bar is positioned
   (e) a collet core having a slit and at least one face sloping towards a slit.

21. A handle assembly for a detachable scalpel blade having a keyed slot, the handle assembly comprising:
   (a) a handle body having a longitudinal axis,
   (b) a blade bar having a portion protruding from the handle body for engaging the blade, and
   (c) a collet having a through bore within which the blade bar is disposed,
   wherein the blade is received in a groove in the protruding portion of the bar,
   wherein the bar is bent and the groove is approximately parallel to the longitudinal axis.

22. The assembly of claim 21, wherein the collet core has a slit within which an end of the blade is received.

23. The assembly of claim 21, wherein the collet core has at least one sloping face for guiding the blade into the slit.

24. The assembly of claim 21, wherein the collet core has a pair of faces sloping toward the slit for guiding the blade end into the slit.

25. The assembly of claim 21, wherein the bore is sized and shaped to permit the bar to move laterally along one axis orthogonal to the longitudinal axis.

26. The assembly of claim 21, wherein the bore has a generally oval cross-sectional shape so that the bar can move laterally within the bore along one axis orthogonal to the longitudinal axis.

27. The assembly of claim 21, wherein the bar is coupled to an actuator for urging the protruding portion of the bar out of the handle assembly for removing the blade from the bar or mounting the blade on the bar.

28. The assembly of claim 27, wherein the actuator is a button attached to a rod attached to the bar.

29. The assembly of claim 28, wherein the rod has two ends and the bar attaches to one end and the button attaches to the other end.

30. The assembly of claim 21, wherein the handle body further comprises:
   (a) a handle grip, and
   (b) a collet core.

31. The assembly of claim 30, wherein the collet has a proximal end and wherein the collet flares at its proximal end.

32. The assembly of claim 21, further comprising a retainer for capturing the rod within the handle body.

33. The assembly of claim 32, wherein the retainer is attached to the handle body with mating threads.

* * * * *